United States Patent [19]
Jang

[11] Patent Number: 5,645,350
[45] Date of Patent: Jul. 8, 1997

[54] HYGIENIC PROTECTING DEVICE FOR AN ELECTRONIC THERMOMETER

[76] Inventor: Chen-Chang Jang, c/o Hung Hsing Patent Service Center P.O. Box 55-1670, Taipei, Taiwan

[21] Appl. No.: 631,164

[22] Filed: Apr. 12, 1996

[51] Int. Cl.$^6$ .......................... G01K 1/08; A61B 1/227; A61B 5/00; A61B 6/00
[52] U.S. Cl. .................. 374/158; 374/209; 128/664; 128/736
[58] Field of Search .................. 374/158, 209; 128/736, 664

[56] References Cited

U.S. PATENT DOCUMENTS

| | | | |
|---|---|---|---|
| Re. 34,599 | 5/1994 | Suszynski et al. | 374/158 |
| 3,833,115 | 9/1974 | Schapker | 374/158 |
| 3,878,836 | 4/1975 | Twentier | 374/158 |
| 4,662,360 | 5/1987 | O'Hara et al. | 128/664 |
| 4,895,164 | 1/1990 | Wood | 128/736 |
| 4,911,559 | 3/1990 | Meyst et al. | 374/158 |
| 5,018,872 | 5/1991 | Suszynski et al. | 374/158 |
| 5,088,834 | 2/1992 | Howe et al. | 374/158 |
| 5,163,418 | 11/1992 | Praden et al. | 128/664 |
| 5,179,936 | 1/1993 | O'Hara et al. | 374/158 |
| 5,411,032 | 5/1995 | Esseff et al. | 128/736 |

FOREIGN PATENT DOCUMENTS

| | | | |
|---|---|---|---|
| 4060443037 | 2/1994 | Japan | 374/158 |
| 0608295 | 12/1978 | Switzerland | 374/158 |

*Primary Examiner*—Diego F. F. Gutierrez

[57] ABSTRACT

A hygienic protecting device for an electronic thermometer includes: a disposable wrapping film wrapped on a front housing portion of an infrared thermometer, a fastening cup member made with a truncated cone shape and disposed about the disposable film on the front housing portion of the thermometer having a probe, the fastening cup member being mounted within the front housing portion for fastening the disposable film on the front housing portion and for preventing contamination when inserting the front housing portion and the probe into a person's ear canal, and a dust-proof thin film wrapped on the probe for shielding the probe for preventing contamination of the probe, with a fastening ring fastening the dust-proof thin film on the probe and a circular contacting ring disposed about the dust-proof thin film and retained between the dust-proof thin film on the probe and an inside wall in the front housing portion within an air space annularly defined between the probe and the front housing portion for minimizing the thermal transfer between the housing portion and the probe and for preventing the influence by ambient temperature, thereby ensuring a reliable temperature measurement in the ear canal of the person to be measured for a reliable and precise measurement of a body temperature.

5 Claims, 4 Drawing Sheets

HYGIENIC PROTECTING DEVICE FOR AN ELECTRONIC THERMOMETER

BACKGROUND OF THE INVENTION

U. S. Pat. No. 4,895,164; 4,911,559 (RE. 34,599); 5,018,872; and 5,411,032 all disclosed a disposable probe cover for use in covering and protecting the probe of a medical infrared thermometer. However, the disposal of the probe cover may waste money and cause a problem of waste disposal. In a family use, the electronic thermometer may be repeatedly used by the same people in the family. After finishing each temperature measurement, the protective probe cover would be disposed and replaced with a complete new cover, increasing family expense and causing a waste disposal problem.

Meanwhile, once the protective probe cover is removed from the conventional thermometers, the radiation guide tube of the probe will be exposed to environmental dust pollution, causing contamination of the probe and possibly influencing the measurement precision of the thermometer.

The present inventor has recognized the drawbacks of the conventional probe assembly of an electronic thermometer, and invented a hygienic protecting device for the electronic thermometer.

SUMMARY OF THE INVENTION

The object of the present invention is to provide a hygienic protecting device for an electronic thermometer including: a disposable wrapping film wrapped on a front housing portion of an infrared thermometer, a fastening cup member made with a truncated cone shape and disposed about the disposable film on the front housing portion of the thermometer having a probe, the fastening cup member being mounted within the front housing portion for fastening the disposable film on the front housing portion and for preventing contamination when inserting the front housing portion and the probe into a person's ear canal, and a dust-proof thin film wrapped on the probe for shielding a radiation guiding hole in the probe for preventing contamination of the probe, with a fastening ring fastening the dust-proof thin film on the probe and a circular contacting ring disposed about the dust-proof thin film and retained between the dust-proof thin film on the probe and an inside wall in the front housing portion within an air space annularly defined between the probe and the front housing portion for minimizing the thermal transfer between the housing portion and the probe and for preventing the influence by ambient temperature thereby ensuring a reliable temperature measurement in the ear canal of the person to be measured for a reliable and precise measurement of a body temperature.

DETAILED DESCRIPTION

Figure 1:
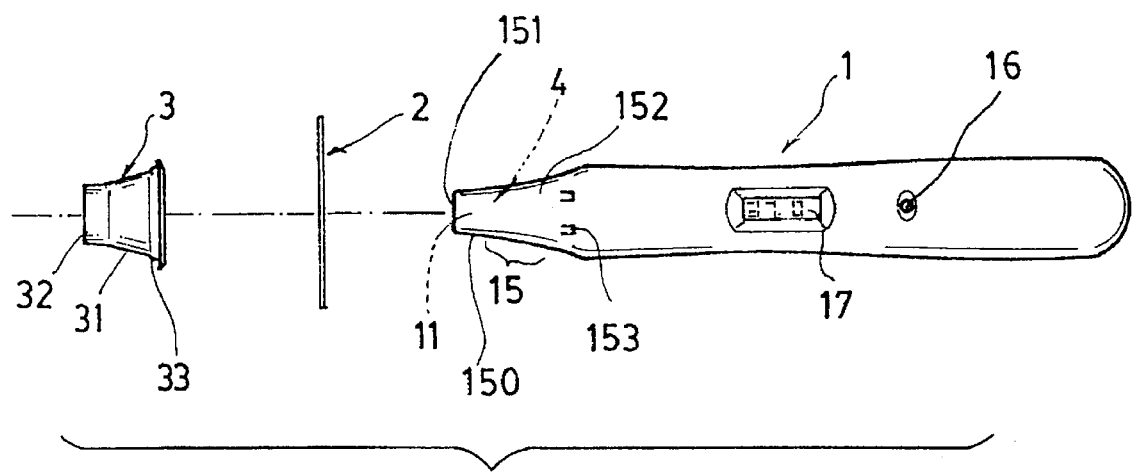
FIG. 1 is an illustration showing the elements in construction of the present invention.
Figure 2:
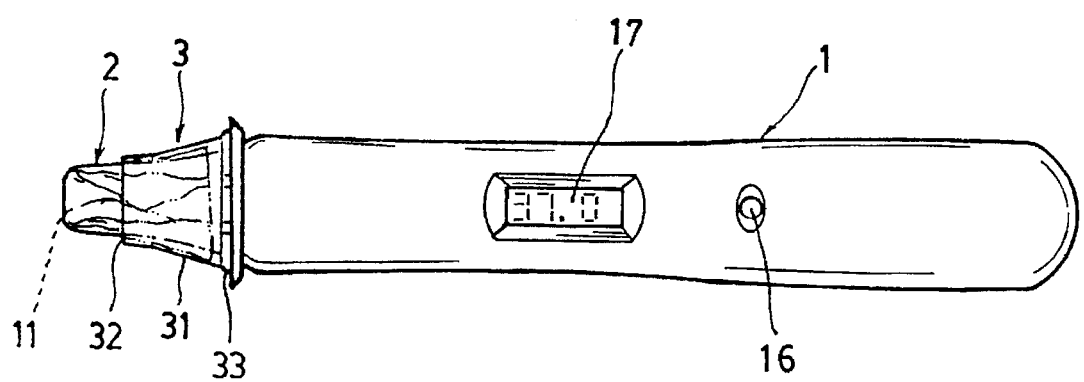
FIG. 2 is an illustration of the present invention when assembled.

As shown in the figures, a preferred embodiment of the present invention comprises: an infrared thermometer 1 having a probe 11 formed in a front housing portion 15 of the thermometer 1, a disposable wrapping film 2 wrapped on the front housing portion 15 for protecting the probe 11 and the front housing portion 15, a fastening cup member 3 disposed around the disposable wrapping film 2 for fastening the wrapping film 2 on the front housing portion 15 of the thermometer 1, and a dust-proof device 4 wrapped on the probe 11 for preventing dust contamination of the probe 11 of the thermometer 1.

Figure 3:
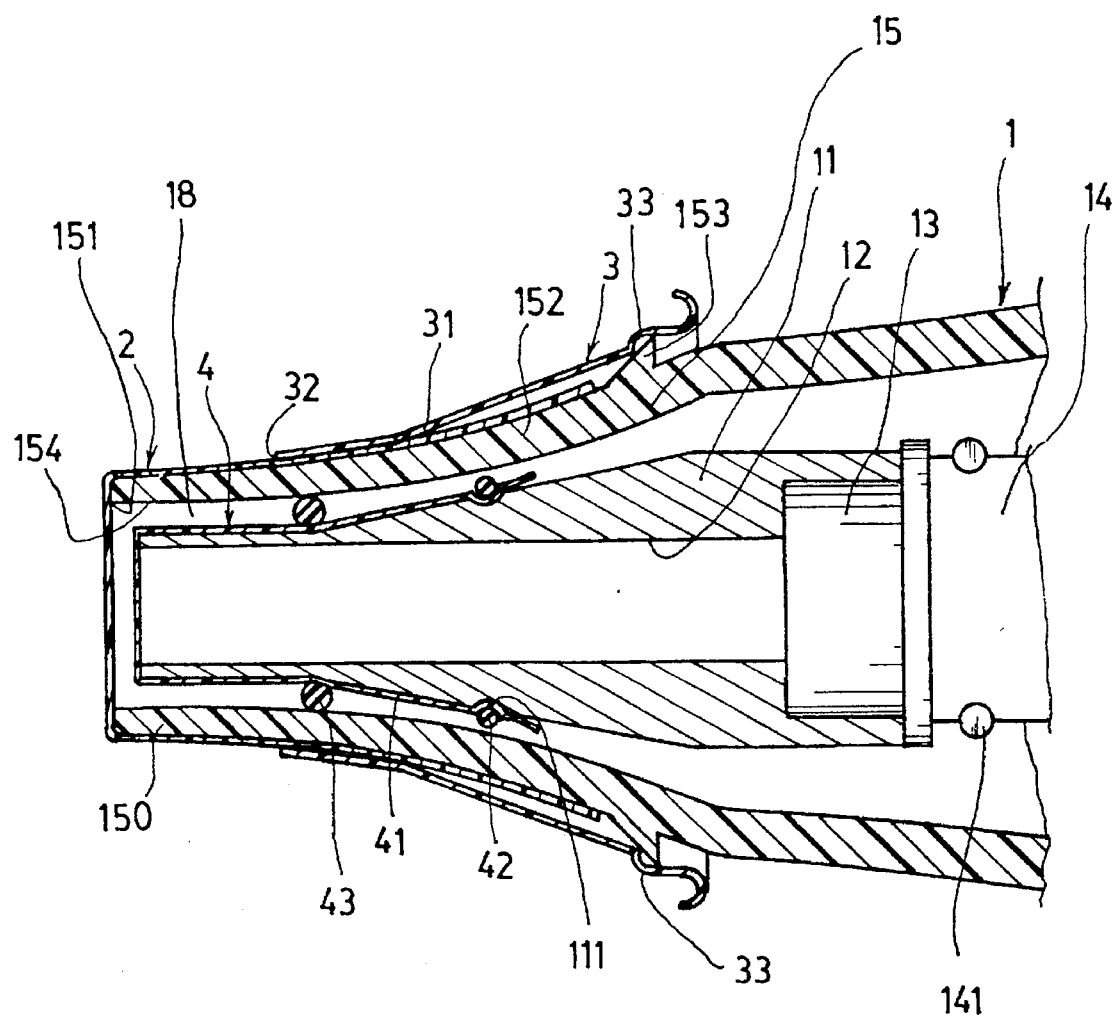
FIG. 3 is a partial sectional drawing of the present invention.
Figure 4:
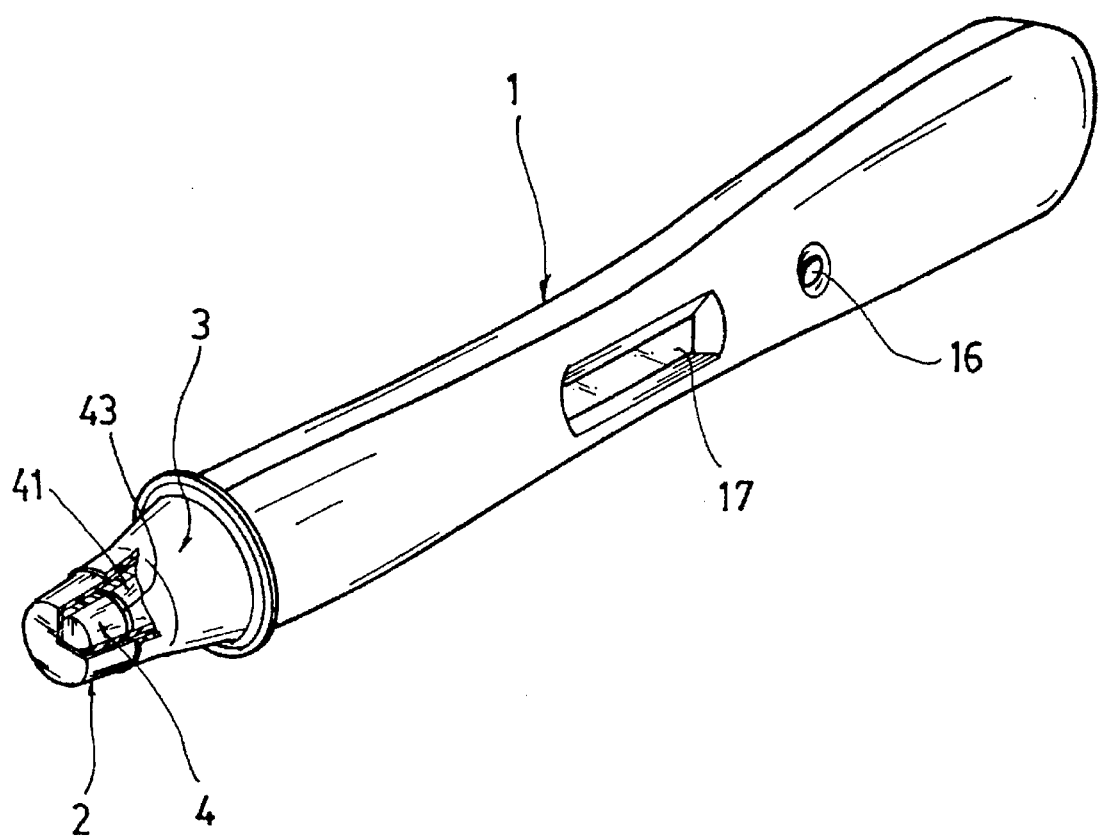
FIG. 4 is a partial cut-away perspective illustration of the present invention.

The infrared thermometer 1 includes: a probe 11 having a generally conical shape and tapered forwardly within a front housing portion 15 formed on a front portion of the thermometer 1, a radiation guiding hole 12 longitudinally formed in the probe 11 for transmitting infrared radiation waves from an ear canal of a person to be measured for his or her body temperature, a sensor 13 formed in a rear portion of the probe 11 for detecting and converting the radiation waves into an electrical signal, a printed circuit board 14 secured on a plurality of stems 141 formed in the thermometer 1 and electrically connected with the sensor 13 for processing the electrical signal as output from the sensor 13 to be a readable digital temperature value which is shown on the LCD display window 17 formed on the thermometer 1, a trigger switch 16 for switching on the thermometer for temperature measurement, and an annular air gap 18 concentrically formed in the front housing portion 15 and defined between an inside wall 154 of the housing portion 15 and the probe 11 wrapped by the dust-proof device 4 as shown in FIG. 3. The front housing portion 15 is also tapered forwardly from the thermometer 1 to surround the probe 11.

The disposable wrapping film 2 may be made of a thin flexible transparent film capable of transmitting infrared radiation waves therethrough, such as poly-ethylene (PE) film, but not limited in this invention.

The wrapping film 2 should have an area large enough to cover the front housing portion 15 of the thermometer.

The disposable wrapping film 2, after being disposed about the front housing portion 15, is fastened on the front housing portion 15 by the fastening cup member 3 generally formed with a truncated cone shape and detachably securable on the front housing portion 15 of the thermometer 1.

The fastening cup member 3 includes: a truncated cone portion 31 slidably engageable with a rear enlarged portion 152 formed on a rear portion of the front housing portion 15 of the thermometer 1, a front cup opening 32 formed in a front end portion of the truncated cone portion 31 and positioned adjacent to a front taper portion 150 formed on a front end portion of the front housing portion 15 of the thermometer 1, and a rear groove 33 annularly formed in a rear end portion of the truncated cone portion 31 and engageable with a projection 153 which has a longitudinal section generally triangular shaped and is formed on a rear portion of the front housing portion 15.

The disposable wrapping film 2 wrapped on the front housing portion 15 will seal a front opening 151 formed in a front end of the front housing portion 15 of the thermometer 1 and the wrapping film 2 will also cover the front housing portion 15 for preventing contamination into the probe of the thermometer by dirt in the ear canal.

The dust-proof device 4 includes: a dust-proof thin film 41 made of transparent and radiation transmissible film materials such as polyethylene film (but not limited in this invention) having an area large enough for sealing the radiation guiding hole 12 in the probe 11, a fastening ring 42 fastening the dust-proof thin film 41 on the probe 11 by packing the thin film 41 between the fastening ring 42 and an annular recess 111 circumferentially formed in a rear portion of the probe 11, and a circular contacting ring 43 annularly retained between the inside wall 154 of the front housing portion 15 of the thermometer 1 and the thin film 41 wrapped on the probe 11, with the circular contacting ring 43 positioned in the annular air gap 18 in front of the fastening ring 42.

The circular contacting ring 43 will stabilize the probe 11 within the front housing portion 15 of the thermometer 1 since the contacting ring 43 is provided as a packing retained in between the inside wall of the front housing portion 15 and the probe 11.

The circular contacting ring 43 will limit the contacting area between the probe 11 and the housing portion 15 of the thermometer 1 to be an annular contacting area as shown in FIG. 3 to minimize the heat transfer including thermal conduction, between the housing portion 15 and the probe because the air gap 18 will serve as a good heat insulative medium for minimizing the influence by the ambient temperature outside the probe 11, thereby and ensuring a reliable temperature measurement by sensing the radiation wave from the ear canal through the guiding hole 12 in the probe 11.

After conducting a temperature measurement by the thermometer 1 of the present invention, the fastening cup member 3 can be removed by disengaging the rear groove 33 in the cup member 3 from the projection 153 on the housing portion 15 and the disposable wrapping film will then be removed and disposed. The cup member 3 can be repeatedly used since the disposable film 2 is cheaper than the cup member 3. For family or personal use, the cup member 3 may not be disposed and can be repeatedly used, thus saving costs and minimizing waste.

The thin film 41 of the dust-proof device 4 will seal the probe 11 for precluding dust entrance into the sensor 13 for ensuring a precise temperature measurement and prolonging the service life of the thermometer.

The infrared thermometer of the present invention may also be substituted with other electronic thermometers by using the same disposable wrapping film, the fastening cup member, and even the dust proof thin film as disclosed in this invention.

The present invention is superior to the conventional electronic thermometer by providing a better protection for the probe of the thermometer and the disposable cover is now replaced with a cheaper disposable film for saving cost and for solving, a problem of waste disposal for better environmental protection. The dirt from the ear canal may only contaminate the front portion of the film, not the truncated cup member. So, the cup member may be repeatedly used, thus saving costs.

The present invention may be modified without departing from the spirit and scope of this invention.

I claim:

1. A hygienic protecting device for an electronic thermometer including a probe formed in the front housing portion of the thermometer for measuring a body temperature and having an air gap defined between said probe and an inside wall in the front housing portion, the hygienic protecting comprising:

a disposable wrapping film made of a thin, flexible, transparent and radiation-wave transmissible film, disposed about the front housing portion of the thermometer;

a fastening cup member having a front portion thereof truncated, said cup member being detachably secured on a rear portion of the front housing portion of the thermometer for fastening the disposable wrapping film on the front housing portion of said thermometer; and a dust-proof device wrapping a probe portion of the probe within the front housing portion of the thermometer for preventing dust contamination of the probe;

and wherein upon finishing a temperature measurement by said thermometer, said disposable wrapping film is removed and disposed, and said cup member is repeatedly used in future temperature measurement.

2. A hygienic protecting device according to claim 1, wherein said fastening cup member include a truncated cone portion, said truncated cone portion including said truncated front portion and being slidably engageable with a rear enlarged portion formed on a rear portion of the front housing portion of the thermometer, a front cup opening formed in a front end portion of the truncated front portion of the truncated cone portion and positioned adjacent to a front taper portion formed on a front end portion of the front housing portion of the thermometer, and a rear groove annularly formed in a rear end portion of the truncated cone portion and engageable with said rear enlarged portion, said rear enlarged portion being a projection.

3. A hygienic protecting device according to claim 1, wherein said disposable wrapping film is wrapped on the front housing portion and seals a front opening formed in a front end of the front housing portion of the thermometer, the wrapping film having an area for covering the front housing portion so as to prevent contamination of the probe of the thermometer.

4. A hygienic protecting device according to claim 1, wherein said dust-proof device includes: a dust-proof thin film made of a transparent and radiation transmissible film having an area for sealing a radiation guiding hole formed in the probe, a fastening ring fastening the dust-proof thin film on the probe by packing the thin film between the fastening ring and an annular recess circumferentially formed in a rear portion of the probe, and a circular contacting ring annularly retained in between the inside wall of the front housing portion of the thermometer and the dust-proof thin film wrapped on the probe, with the circular contacting ring positioned in an annular air gap in front of the fastening ring.

5. A hygienic protecting device according to claim 4, wherein said circular contacting ring defines an annular contacting area between the probe and the inside wall of the front housing portion of the thermometer to minimize the heat transfer between the front housing portion and the probe, and wherein the heat transfer is also minimized by the air gap defined between the probe and the inside wall of the front housing portion.

* * * * *